(12) United States Patent
Ward (10) Patent No.: US 9,937,301 B2
(45) Date of Patent: Apr. 10, 2018

(54) TAMPER EVIDENT SYRINGE TIP CAP

(71) Applicant: BAXTER CORPORATION ENGLEWOOD, Englewood, CO (US)

(72) Inventor: Brian William Ward, Littleton, CO (US)

(73) Assignee: BAXTER CORPORATION ENGLEWOOD, Englewood, CO (US)

( * ) Notice: Subject to any disclaimer, the term of this patent is extended or adjusted under 35 U.S.C. 154(b) by 89 days.

(21) Appl. No.: 15/179,643

(22) Filed: Jun. 10, 2016

(65) Prior Publication Data

US 2017/0354792 A1   Dec. 14, 2017

(51) Int. Cl.
*A61M 5/00* (2006.01)
*A61M 5/50* (2006.01)
*A61M 5/32* (2006.01)
*A61M 39/10* (2006.01)

(52) U.S. Cl.
CPC ........ *A61M 5/5086* (2013.01); *A61M 5/3202* (2013.01); *A61M 39/1011* (2013.01)

(58) Field of Classification Search
CPC .. A61M 2005/3104; A61M 2005/3114; A61M 5/1782; A61M 5/3134; A61M 5/3202; A61M 5/50; A61M 5/5086
See application file for complete search history.

(56) References Cited

U.S. PATENT DOCUMENTS

| | | | |
|---|---|---|---|
| 6,585,391 B1* | 7/2003 | Koch | F21L 4/005 200/512 |
| 6,991,002 B2 | 1/2006 | Osborne et al. | |
| 7,632,244 B2* | 12/2009 | Buehler | A61M 5/50 206/726 |
| 8,353,869 B2 | 1/2013 | Ranalletta et al. | |
| 2010/0324502 A1* | 12/2010 | Guala | A61M 5/3134 604/236 |
| 2011/0015578 A1* | 1/2011 | Lowke | A61M 5/5086 604/192 |
| 2014/0358078 A1* | 12/2014 | Fischer | A61M 5/3134 604/111 |

* cited by examiner

*Primary Examiner* — Rebecca E Eisenberg
(74) *Attorney, Agent, or Firm* — K&L Gates LLP (57) ABSTRACT

A tamper-evident syringe tip cap is provided and includes an outer housing with an outer shell, and a tip cover secured to an upper end of the outer shell. An inner core has a female Luer lock fitting, a spindle projecting vertically from the fitting, and a sleeve matingly engaging the spindle and being constructed and arranged for releasably securing the outer housing to the inner core. The outer housing is movable relative to the inner core between a first, pre-activated position and a second, activated position.

18 Claims, 8 Drawing Sheets

TAMPER EVIDENT SYRINGE TIP CAP

BACKGROUND

The present invention relates to caps for syringes used in medical treatments and procedures, and more specifically to a tamper evident cap for such a syringe.

It is common for medical syringes to be pre-loaded with a medical solution, such as medicine, saline or a constituent of a medical treatment that is designed to be mixed with another constituent prior to administration to the patient. Medical practitioners including doctors, nurses and medical technicians are concerned that the contents of these syringes remain in the syringe prior to administration, and also that the contents remain sterile and unadulterated prior to their desired administration.

Thus, there is a need for a cap for a medical syringe that addresses these objectives.

SUMMARY

The above-listed needs are met or exceeded by the present tamper evident syringe tip cap, engageable on a conventional syringe male Luer lock, which features a visible tamper evident feature, that once breached, prevents reuse of the cap, and provides a visible condition indicator to the medial practitioner that the syringe has been accessed and is no longer sterile. In addition, the cap features a two-stage mechanism including a pre-activated position or mode, and an activated (tamper evident) position or mode. In the pre-activated mode, the cap is installed and removable via the male Luer threads on the syringe. In the tamper-evident mode, an outer housing of the cap must be removed in order to access and remove an inner core from the syringe.

The main components of the cap include an outer housing, a dome-like tip cover frangibly connected to an upper edge of the housing, and an inner core including a female Luer fitting and a vertically projecting spindle. A sleeve fits over the spindle to retain the outer shell on the spindle. Axially spaced grooves on the sleeve engage clips on the tip cover. The relative position of the sleeve and the tip cover provide a visual indication of which of the two modes the cap is in. Another feature of the present cap is that the first mode is also referred to as a shipping position, and the second position is a free-spinning position, in which the outer shell spins or rotates axially relative to the inner core. In the latter position, the female Luer connection is obscured by a lower end of the outer shell, preventing access by a user. Also, an effort by a user to remove the cap will cause the tip cover to dislodge from the outer shell, providing a visual indication that the cap has been tampered with.

More specifically, a tamper-evident syringe tip cap is provided and includes an outer housing with an outer shell, and a tip cover secured to an upper end of the outer shell. An inner core has a female Luer lock fitting, a spindle projecting vertically from the fitting, and a sleeve matingly engaging the spindle and being constructed and arranged for releasably securing the outer housing to the inner core. The outer housing is movable relative to the inner core between a first, pre-activated position and a second, activated position.

In another embodiment, a tamper-evident syringe tip cap is provided, including an outer housing including an outer shell, and a tip cover secured to an upper end of the outer shell. An inner core has a female Luer lock fitting, a spindle projecting vertically from the fitting, and a sleeve matingly engaging the spindle and being constructed and arranged for releasably securing the outer housing to the inner core. The outer housing is movable relative to the inner core between a first, pre-activated position in which an upper end of the sleeve axially projects from the tip cover, a second, activated position in which the upper end of the sleeve is flush with the tip cover and the outer housing axially rotates relative to the inner core, and a third, removed position, in which the outer housing is pulled axially over the sleeve.

DETAILED DESCRIPTION

Figure 1:
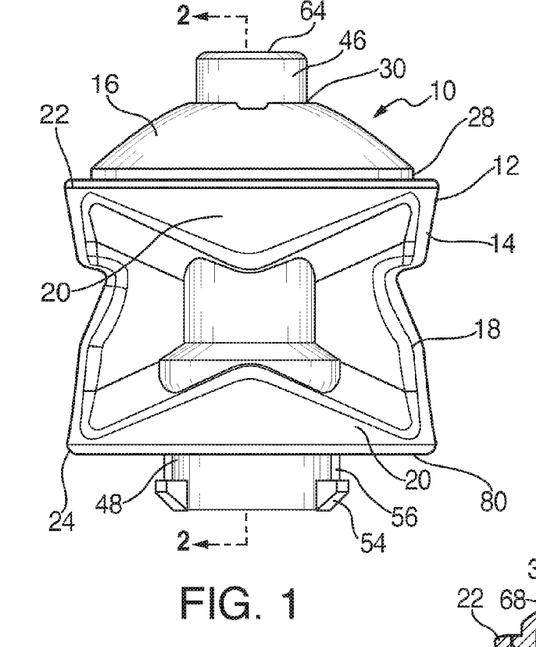
FIG. 1 is a front elevation of the present tip cap in a shipping position.
Figure 2:
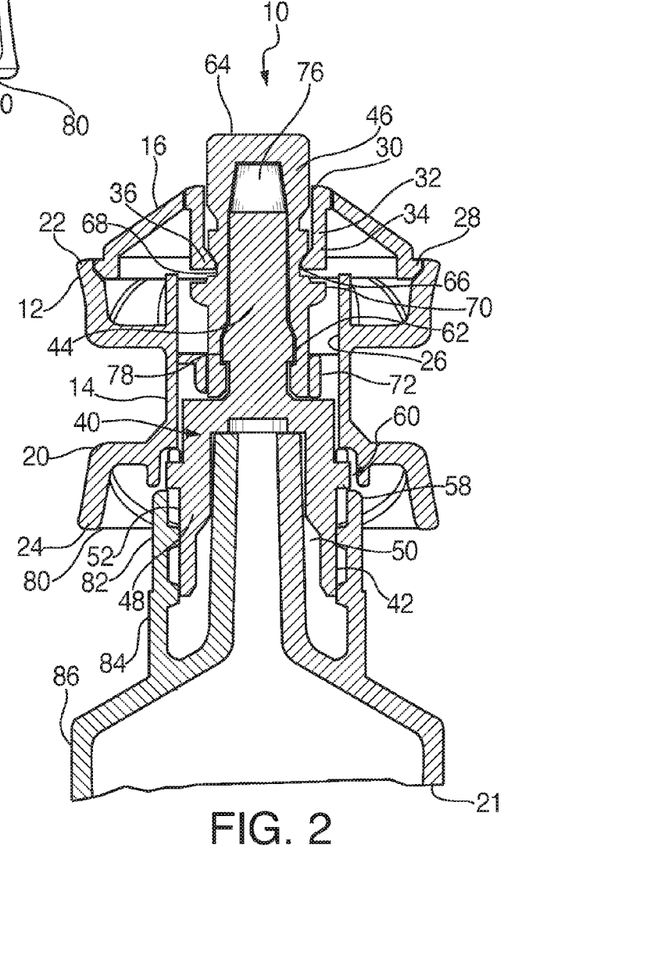
FIG. 2 is a cross-section taken along the line 2-2 and in the direction generally indicated.
Figure 3:
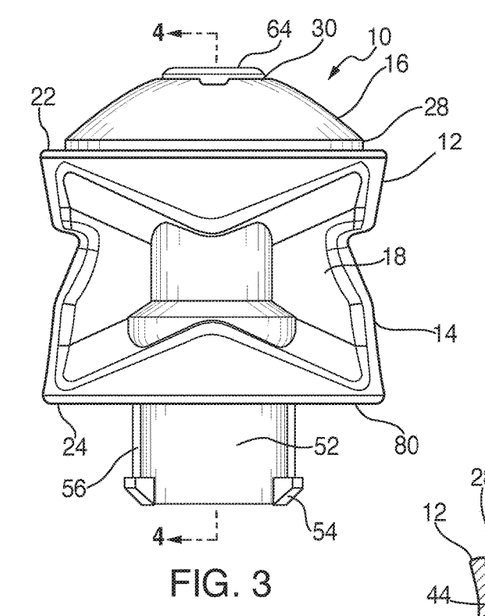
FIG. 3 is a front elevation of the present tip cap in an engaged position on the syringe.
Figure 4:
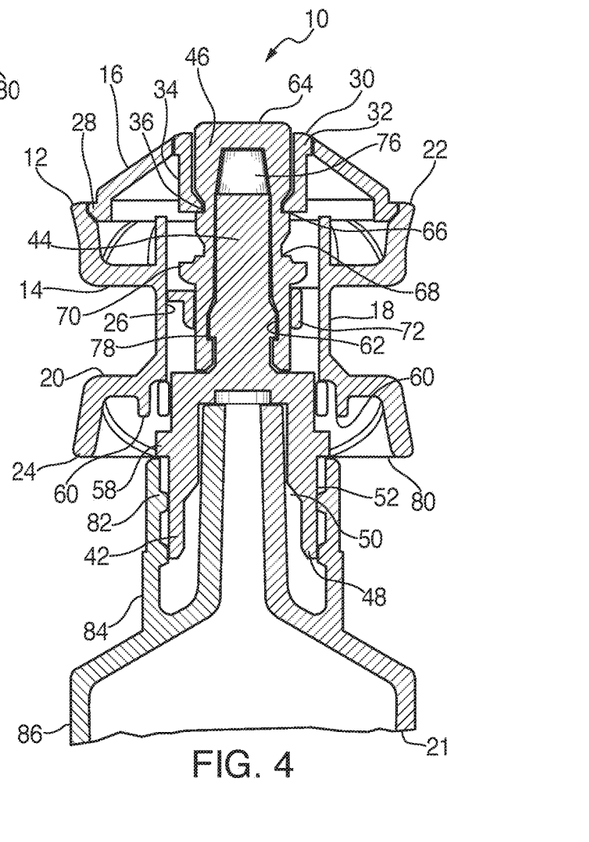
FIG. 4 is a cross-section taken along the line 4-4 of FIG. 3 and in the direction indicated.

Referring now to FIGS. 1-4, the present tamper-evident syringe tip cap is generally designated 10 and includes an outer housing 12 formed by an outer shell 14 and a tip cover 16. While other materials are contemplated, the outer shell 14 is preferably made of polystyrene, chosen for its low friction surface which facilitates automation, and relatively high tensile strength for creating frangible features. An exterior or outer surface 18 of the outer shell 14 is provided with handling or gripping formations 20 configured for engagement by automated handling equipment or by manipulation by medical technicians. It is contemplated that the gripping formations 20 are provided with a variety of shapes depending on the desired system for manually or automatically handling the cap 10 and the associated syringe 21 (FIGS. 2 and 4). Syringe construction is fairly standard in the industry and well known to those of ordinary skill in the art.

Also included on the outer shell 14 is an upper end 22 and an opposite lower or bottom end 24 forming a skirt. The skirt 24 of the outer shell 14 is constructed and arranged to accommodate a Perfusor® syringe. The outer shell 14 defines an inner passageway 26 extending axially through the entire shell from the upper end 22 to the lower end 24. In the preferred embodiment, the passageway 26 is generally cylindrical, however other shapes are contemplated. A feature of the outer housing 12 is that the tip cover 16 is frangibly secured to the upper end 22 such that unwanted or unauthorized manipulation of the cap 10 as described in further detail below causes detachment of the tip cover 16 which provides a visual indication of tampering.

Figures 5, 6:
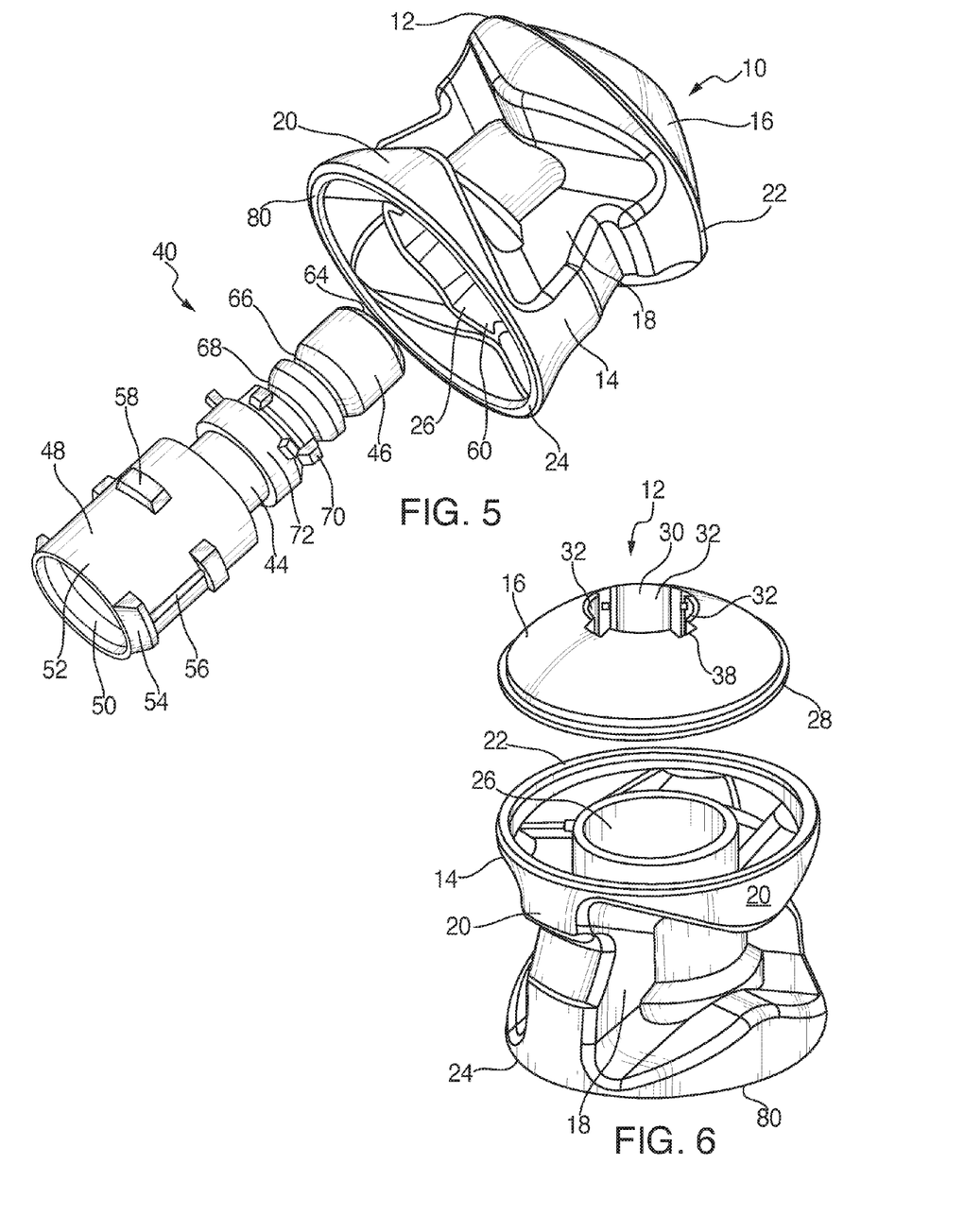
FIG. 5 is an exploded perspective view of the present cap.
FIG. 6 is a fragmentary top perspective exploded view of the present cap.
Figure 7:
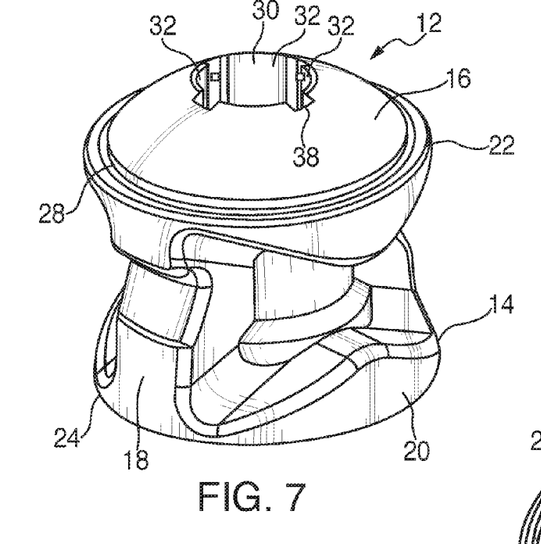
FIG. 7 is a fragmentary perspective view of the cap of FIG. 6.
Figure 8:
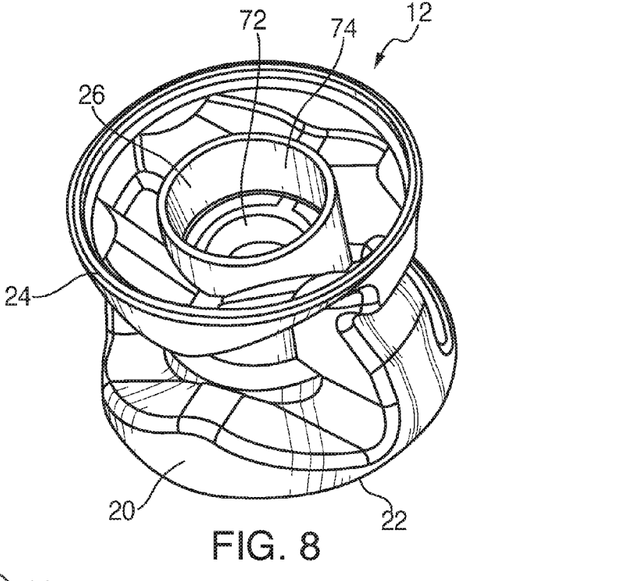
FIG. 8 is a bottom perspective view of the present cap.
Figure 9:
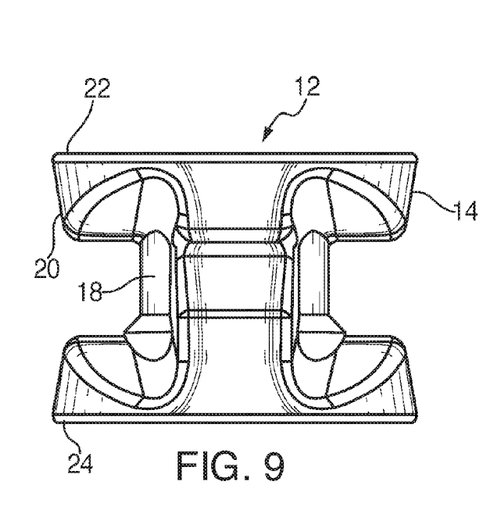
FIG. 9 is a side elevation of the cap of FIG. 7.

Referring now to FIGS. 1-4, 6, 7 and 13, the tip cover 16 has a generally dome shape, with a peripheral edge 28 that is scored, reduced in thickness or otherwise fabricated or molded to facilitate detachment of the cover from the outer shell 14. While other materials are contemplated, the tip cover 16 is preferably made of polystyrene, chosen for its ability to bond to the outer shell 14, and potentially stress-induced color change. Polystyrene is also desirable due to its high tensile strength, utilized in the one-way snap features. More specifically, the tip cover 16 and the outer shell 14 are secured, as by solvent bonding, being snap-fit, or ultrasonically bonded or welded, all of which are well known in the art. These techniques are preferred due to the inability to mold the tip cover 16 to the outer shell 14 as one component. Regardless of the type of attachment, the outer housing assembly 12 is constructed to display evidence that it has been compromised, or removed and reinstalled by detachment of the tip cover 16 from the outer shell 14. Such indications include color change in the form of stress marks, or actual breakage or separation of the tip cover 16 from the outer shell 14 (FIG. 6).

In addition, the tip cover 16 has a central aperture 30 defined in part by depending snaps 32. Preferably, the depending snaps 32 have an axially extending body 34 with a radially inwardly projecting rib 36. Also, the snaps are circumferentially spaced from each other by slots 38 (best seen in FIG. 13) to promote a lateral flexing or reciprocating action as will be described below. The dome-shaped exterior surface of the tip cover 16 provides an interior space for the one-way snaps 32, and also aids in forward travel throughout automation.

Referring now to FIGS. 1-5 and 14-18, an inner core 40 of the present cap 10 provides a reference point relative to which the outer housing 12 is axially slidable depending on the mode or position of the cap 10. More specifically, the outer housing 12 is movable relative to the inner core 40 between a first, pre-activated position or mode (FIGS. 1 and 2) and a second, activated position or mode (FIGS. 3 and 4). The inner core 40 has a generally cylindrical female Luer lock fitting 42, a spindle 44 projecting vertically or axially from the fitting, and a sleeve 46 matingly engaging the spindle and being constructed and arranged for releasably securing the outer housing 12 to the inner core.

The Luer lock fitting 42 includes a female housing 48 with an ISO compatible Luer taper 50, and an external surface 52 with male threads 54 for engaging a complementary formation on the syringe 21 as is well known in the art. Thin, axially projecting crush-ribs 56 on the exterior surface 52 prevent spin-off of the male syringe relative to the inner core 40. A plurality, and preferably four peripherally spaced, rectangular bosses or splines 58 project radially from the female housing 48 and are constructed and arranged to engage complementary skirt recesses or female pockets 60 on the outer shell 14. This latter construction connects the inner core 40 with the outer housing 12 for common rotation when the cap 10 is in the shipping position (FIGS. 1 and 2) to facilitate threading or unthreading the cap upon the syringe 21.

Referring now to FIGS. 2, 4, 15 and 16, the vertically projecting spindle 44 provides the mounting structure for the sleeve 46, is preferably integrally molded with the inner core 40 and has a radially projecting ring 62 that forms a snap feature for retaining the sleeve 46 in position to secure the outer housing 12 to the inner core 40 as described below. The holding force of the ring 62 is greater than the frangible force needed to remove the tip cover 16. In addition, the complementary construction of the spindle 44 and the sleeve 46 makes the present cap 10 difficult to remove without the use of tools. In the preferred embodiment, the spindle 44 has an axial height approximately equal to a height of the female housing 48, however other relative dimensions are contemplated.

Referring now to FIGS. 2, 4, 5, 13, 14, 15, 17 and 18, as discussed above, the sleeve 46 retains the outer housing 12 to the inner core 40 such that the outer housing is sandwiched between the sleeve and the spindle 44. The present cap 10 is assembled by placing the outer housing 12 over the spindle 44 so that the spindle projects through the central aperture 30 in the tip cover 16. Next, the sleeve 46 is inserted into the central aperture 30 and snaps onto the spindle 44. During insertion, the lugs 70 on the spindle 44 are accommodated by the slots 38 between adjacent snaps 32. Below a closed sleeve tip 64 are at least a pair of upper and lower annular notches or grooves respectively numbered 66, 68 which create the positions or modes for the cap 10. The upper groove 66 is closer to the sleeve tip 64, and the lower groove 68 is farther from the sleeve tip. At this point, the ribs 36 of the snaps 32 on the tip cover 16 engage the respective grooves 66, 68. The lower notch 68 is a landing for the default, a first "pre-activated," "shipping" or "threads engaged" mode or position that allows the user to thread or unthread the cap 10 from the syringe 21 (FIG. 2). Also, in this position, the sleeve tip 64 protrudes axially from the dome shape of the tip cover 16, and provides an axial and longitudinal datum for an automated handling device (not shown), as well as a visual indication to users that the cap 10 is in the shipping position.

When the snap ribs 36 engage the upper notch 66, the cap 10 is positioned in a second, "activated," "tamper evident" or "free-spin" mode, wherein, through axial displacement of the outer housing 12 relative to the inner core 40, the splines 58 are disengaged from the pockets 60. In this position, the sleeve tip 64 is flush with the dome of the tip cover 16 (FIG. 4), and the outer housing 12 is axially rotatable or spinnable relative to the inner core 40 due to the axial displacement and disengagement of the splines 42 from the pockets 60. When engaged, threading and unthreading with a male Luer lock syringe is available.

Referring now to FIGS. 2, 4, 5, 8, 11, 12, 19 and 20, axially below the notches 66, 68 are a plurality and preferably four small bosses or lugs 70 are positioned on the sleeve 46 in a cross-pattern for engaging at least one frangible ring 72 of the outer shell 14. Preferably, the ring 72 is aligned with the inner passageway 26 and is secured to an inner wall 74 of the passageway. One function of the frangible ring 72 is to guide the sleeve 46 during insertion upon the spindle 44. The relatively small size of the lugs 70 facilitates their passage through the central aperture 30 of the tip cover 16 during assembly. In the preferred embodiment, the aperture 30 is cross-shaped by virtue of the position and peripheral spacing of the four snaps 32, and allows the outer housing 12 to be installed onto the inner core 40. When the splines 58 are disengaged from the pockets 60, the outer shell 14 will spin freely about the core, retained by the frangible ring 72.

An inherent releasable biasing force of the tip cap snaps 32 permits the ribs 36 to exert an internal radial force on the sleeve grooves 66, 68 as the outer housing 12 is moved axially relative to the inner core 40 when the outer housing 12 is moved axially relative to the inner core 40 to the "activated" position. Also, in the activated position or mode, the passageway 26 provides a bearing for the outer shell 14 to rotate freely about the inner core 40. The length of the snaps 32 is long enough to included adequate distance between the corresponding position steps.

Figures 10, 11, 12:
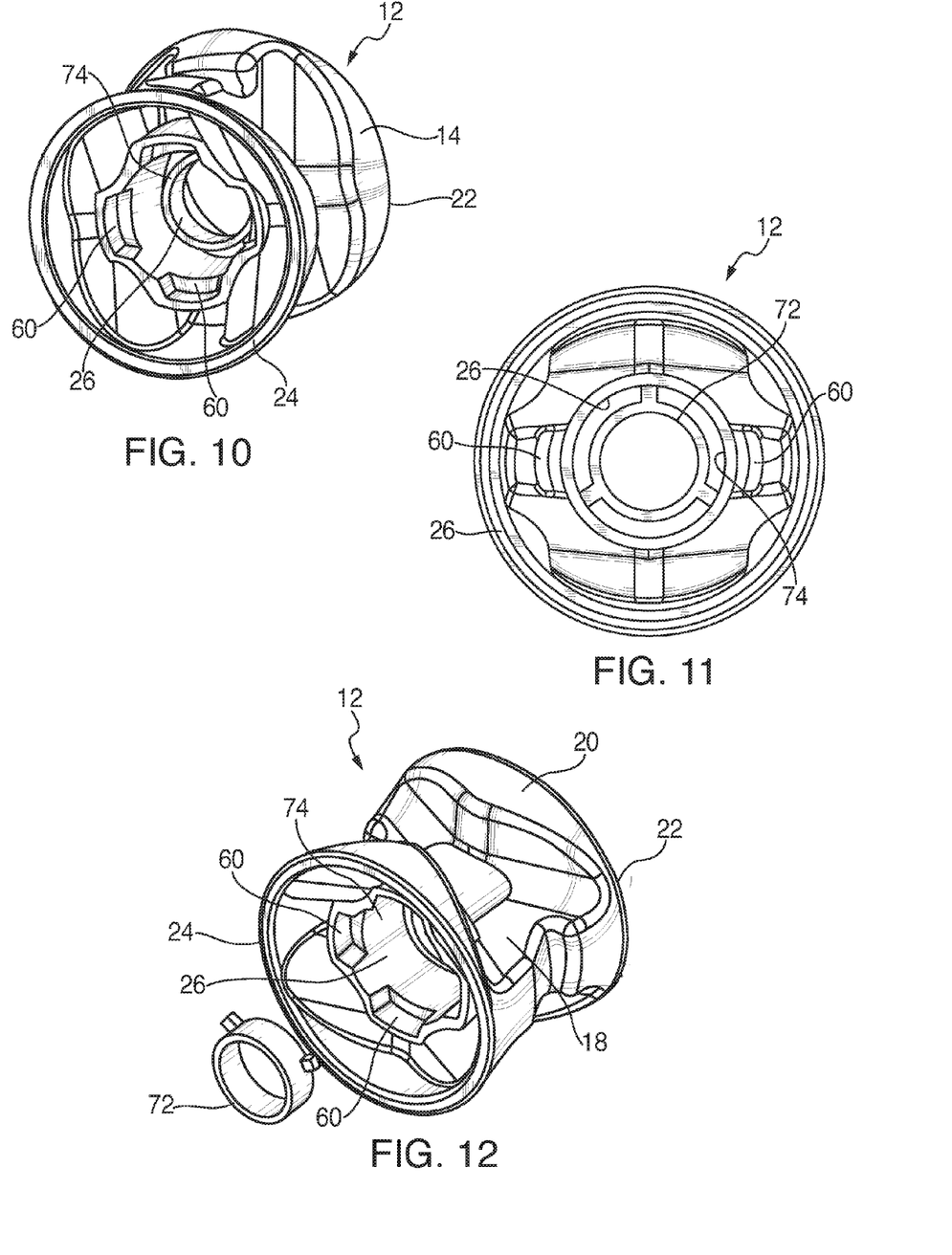
FIG. 10 is a fragmentary bottom perspective view of the present cap.
FIG. 11 is a bottom plan view of the cap of FIG. 8.
FIG. 12 is a fragmentary exploded perspective view of the cap of FIG. 8.
Figure 13:
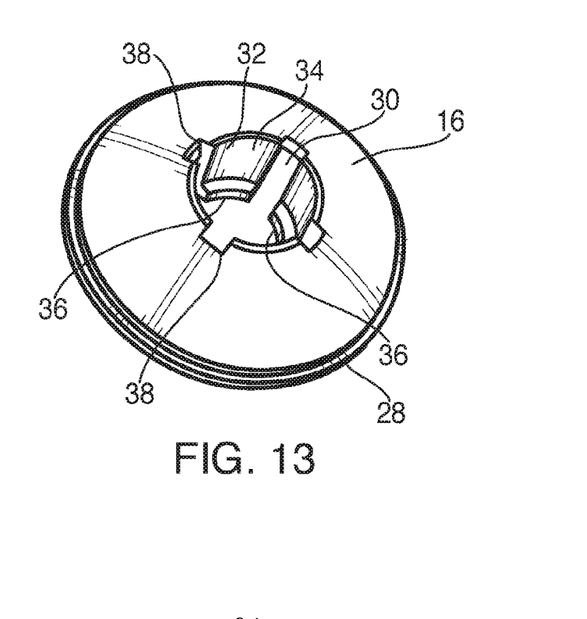
FIG. 13 is a top perspective of the present tip cover.
Figure 14:
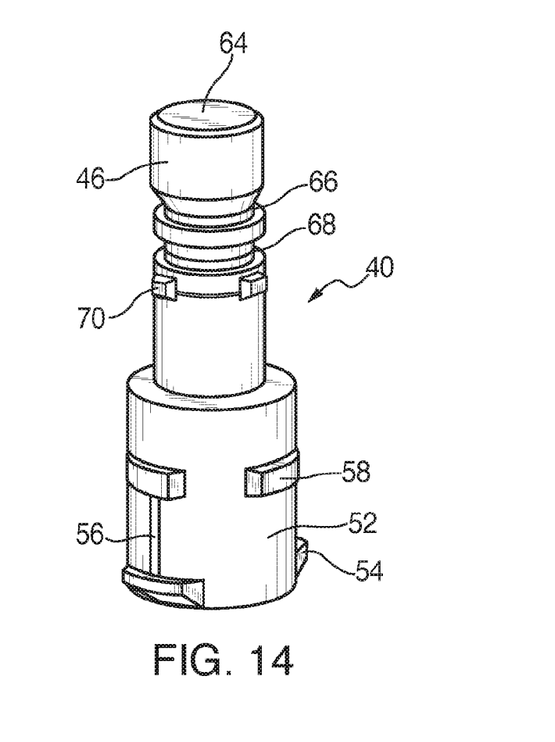
FIG. 14 is a front perspective view of the present inner core, being a combined Luer lock and spindle.
Figure 15:
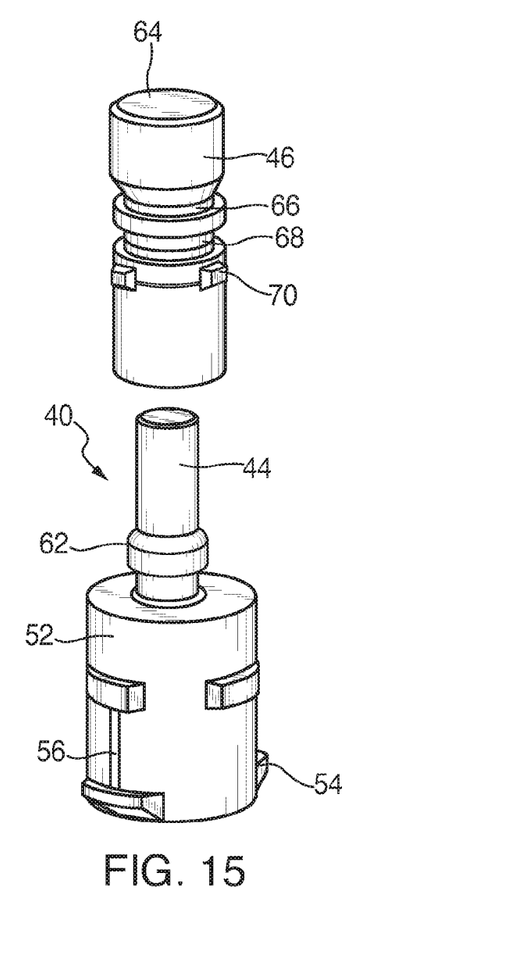
FIG. 15 is an exploded perspective view of the structure shown in FIG. 14.
Figure 16:
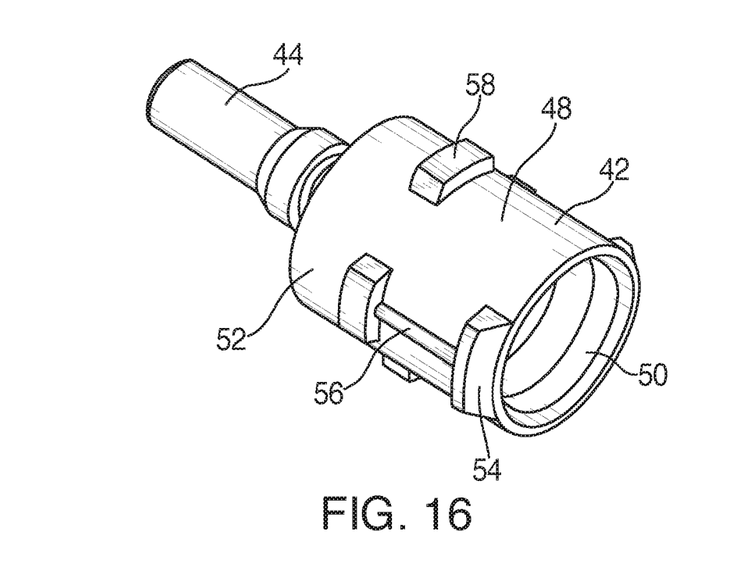
FIG. 16 is an enlarged perspective view of the present female Luer fitting of FIG. 15.
Figure 17:
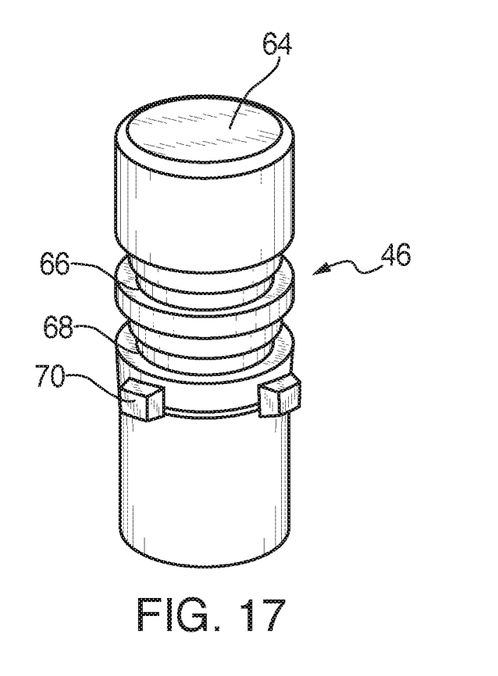
FIG. 17 is a top perspective view of the present sleeve.
Figure 20:
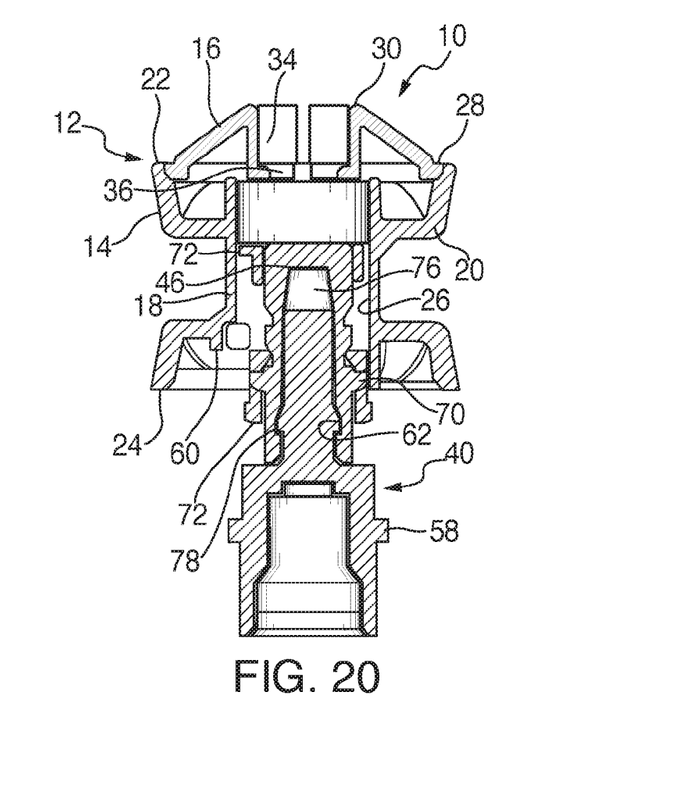
FIG. 20 is a cross-section taken along the line 20-20 of FIG. 19 and in the direction generally indicated.

As the cap 10 is removed from the syringe, with the outer housing 12 being pushed away from the syringe and moved relative to the inner core 40, the lugs 70 engage and detach the frangible ring 72 from the outer housing (FIGS. 12, 20). The frangible ring 72 is designed to retain the outer shell 14 in a free-spinning state until the user removes it from the core. When the user removes the outer shell 14, by pushing the shell axially away from the syringe, the frangible ring 72 is detached, and the shell is discarded.

Figure 18:
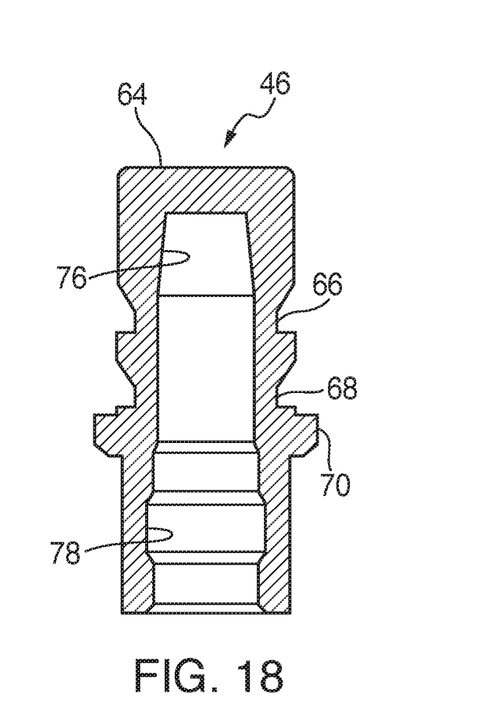
FIG. 18 is a vertical cross-section of the sleeve of FIG. 17.

Referring now to FIG. 18, the sleeve 46 is also provided with an internal cavity 76 dimensioned to matingly engage the spindle 44, and includes an annular recess 78 configured for receiving the spindle ring 62.

Referring now to FIGS. 2, 3 and 4, when the cap 10 is in the "pre-activated" or shipping position (FIG. 2), a feature of the outer shell 14 is that the skirt 24 has a lower surface 80 that is in close proximity to an upper edge 82 of an annular collar 84 of the syringe 21. As is known in the art, the annular collar 84 surrounds a male Luer tip 86 which, upon engagement of the cap 10 with the syringe 21, extends into the Luer taper 50 in the female Luer fitting 48. Also, the annular collar 84 threadably engages the threads 54. In this "pre-activated" position, a user can readily thread the syringe 21 onto the female fitting 48.

Referring now to FIG. 4, when the cap 10 is in the "activated" position, with the outer housing 12 displaced vertically, and rotating relative to the inner core 40, the skirt 24 sufficiently obscures and shields the inner core from manual removal and reinstallation. More specifically, the skirt 24 creates an annular obstruction to a user attempting to grip the inner core to unthread and disengage the syringe 21 from the cap 10. Further, with the tip cover 16 obscuring the sleeve tip 64, a user is also unable to obtain a sufficiently positive grip on the sleeve to attempt to unthread the syringe 21 from the cap 10. The present cap construction further hampers a user tampering with the syringe in the activated position because the free-spinning condition of the outer shell 14 relative to the inner core 40. Any torque applied to the outer shell 14 in this position does not enable the user to apply corresponding torque to the inner core 40 with the ultimate goal of unthreading the annular collar 84. The crush ribs 56 further secure the annular collar 84 upon the inner core 40 and resist unthreading. Accordingly, in the activated position of FIGS. 3 and 4, the only way to obtain and apply sufficient torque to the cap 10 to unthread it from the syringe 21 is to completely pull off the outer housing 12, providing a clear visual indication of tampering, or to push the outer housing 12 back to the pre-activated position so that the splines 58 re-engage the pockets 60 so that the outer housing and the inner core 40 rotate together. However, in the latter situation, the tip cover 16 will detach or deform relative to the outer shell, again providing a visual indication of tampering. As such, this structure provides another tamper resistant feature.

Figure 19:
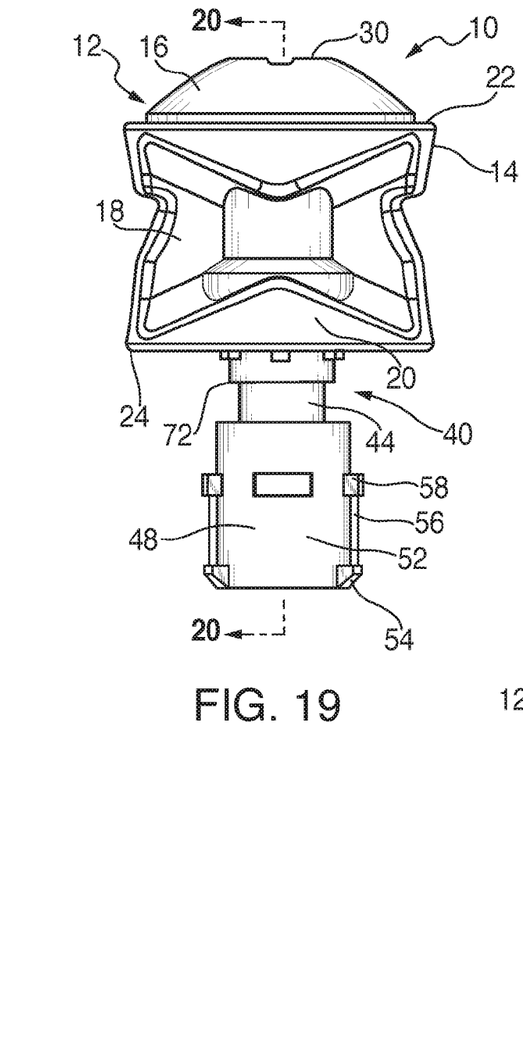
FIG. 19 is a front elevation of the present cap in the removed position.

Referring now to FIGS. 19 and 20, in addition to the "pre-activated" and the "activated" positions of FIGS. 1-4, the present cap 10 has a third, "removed" position in which the outer housing 12 is pulled axially over the sleeve. This position is achieved by the user, when removing the present cap 10 from the syringe prior to using the syringe. By pulling the outer housing 12 upward away from the syringe, the lugs 70 on the sleeve 46 detach the frangible ring 72, and expose the Luer lock housing 48 so that the user can remove the housing from the syringe.

While a particular embodiment of the present tamper-evident syringe tip cap has been described herein, it will be appreciated by those skilled in the art that changes and modifications may be made thereto without departing from the invention in its broader aspects and as set forth in the following claims.

The invention claimed is:

1. A tamper-evident syringe tip cap, comprising:
   an outer housing including an outer shell, and a tip cover secured to an upper end of said outer shell;
   an inner core having a female Luer lock fitting, a spindle projecting vertically from said fitting, and a sleeve matingly engaging said spindle and being constructed and arranged for releasably securing said outer housing to said inner core; and
   said outer housing being movable relative to said inner core between a first, pre-activated position and a second, activated position.

2. The cap of claim 1, wherein said tip cover is frangibly secured to said upper end of said outer shell.

3. The cap of claim 1 wherein said tip cover has an aperture defined in part by depending snaps, and said sleeve is provided with at least two axially spaced grooves configured to be engaged by said snaps in each of said two positions.

4. The cap of claim 3 wherein said at least two axially spaced grooves include a first, pre-activated groove located farther from a sleeve tip, and a second, activated groove located closer to said sleeve tip with respect to said first groove.

5. The cap of claim 1 wherein when said cap is in said pre-activated position a sleeve tip projects vertically past an exterior surface of said tip cover, and when said cap is in said activated position, said sleeve tip is generally flush with said exterior surface of said tip cover.

6. The cap of claim 1 wherein said outer housing and said inner core are constructed and arranged so that when said cap is in said activated position, said outer housing is axially rotatable relative to said inner core.

7. The cap of claim 6 wherein said female Luer fitting has an exterior with at least one radially extending spline constructed and arranged for engaging corresponding skirt recesses on said outer shell for preventing rotation of said outer housing relative to said inner core in said pre-activated position, and upon said cap being moved to said activated position, said at least one spline is axially displaced from said skirt recesses to permit relative rotation of said outer housing relative to said inner core.

8. The cap of claim 1 wherein said outer shell has a passageway provided with at least one frangible ring frangibly secured to an inner wall of said passageway, and said sleeve includes at least one radially extending lug constructed and arranged for being in operational relationship to said at least one frangible ring in said pre-activation position, and as said cap is removed from the syringe, with said outer housing being pushed away from the syringe and moved relative to said inner core, said lugs engage and detach said frangible ring from said outer housing.

9. The cap of claim 1 wherein said outer housing is sandwiched between said sleeve and said spindle for retaining said outer housing to said inner core.

10. The cap of claim 1 wherein said outer housing is provided with a skirt a lower end opposite said tip cover, said skirt constructed and arranged to shield a Luer lock formation on said inner core from manual removal and re-installation.

11. The cap of claim 1, wherein unwanted manipulation of said outer housing causes said tip cover to detach from said outer shell, indicating tamping.

12. The cap of claim 1, further including a third, removed position in which said outer housing is pulled axially over said sleeve.

13. A tamper-evident syringe tip cap, comprising:
an outer housing including an outer shell, and a tip cover secured to an upper end of said outer shell;
an inner core having a female Luer lock fitting, a spindle projecting vertically from said fitting, and a sleeve matingly engaging said spindle and being constructed and arranged for releasably securing said outer housing to said inner core; and
said outer housing being movable relative to said inner core between a first, pre-activated position in which an upper end of said sleeve axially projects from said tip cover, a second, activated position in which said upper end of said sleeve is flush with said tip cover and said outer housing axially rotates relative to said inner core, and a third, removed position, in which said outer housing is pulled axially over said sleeve.

14. The cap of claim 13 wherein said tip cover has an aperture defined in part by depending snaps, and said sleeve is provided with at least two axially spaced grooves configured to be engaged by said snaps in each of said pre-activated and said activated positions.

15. The cap of claim 14 wherein said at least two axially spaced grooves include a first, pre-activated groove located farther from a sleeve tip, and a second, activated groove located closer to said sleeve tip with respect to said first groove.

16. The cap of claim 13 wherein said female Luer fitting has an exterior with at least one radially extending spline constructed and arranged for engaging corresponding skirt recesses on said outer shell for preventing rotation of said outer housing relative to said inner core in said pre-activated position, and upon said cap being moved to said activated position, said at least one spline is axially displaced from said skirt recesses to permit relative rotation of said outer housing relative to said inner core.

17. The cap of claim 13 wherein said outer shell has an inner passageway provided with at least one frangible ring frangibly secured to an inner wall of said passageway, and said sleeve includes at least one radially extending lug constructed and arranged for being in operational relationship to said at least one frangible ring in said pre-activation position, and as said cap is removed from the syringe, with said outer housing being pushed away from the syringe and moved relative to said inner core, said lugs engage and detach said frangible ring from said outer housing.

18. The cap of claim 13 wherein said outer housing is sandwiched between said sleeve and said spindle for retaining said outer housing to said inner core.

\* \* \* \* \*